United States Patent [19]

Shichman

[11] Patent Number: 4,488,523
[45] Date of Patent: Dec. 18, 1984

[54] FLEXIBLE, HYDRAULICALLY ACTUATED DEVICE FOR APPLYING SURGICAL FASTENERS

[75] Inventor: Daniel Shichman, Trumbull, Conn.

[73] Assignee: United States Surgical Corporation, Norwalk, Conn.

[21] Appl. No.: 423,467

[22] Filed: Sep. 24, 1982

[51] Int. Cl.³ .............................................. A61B 17/04
[52] U.S. Cl. ................................ 128/334 R; 128/305; 227/DIG. 1
[58] Field of Search ........... 128/334 R, 303 R, 334 C, 128/305, 356, 335; 227/DIG. 1

[56] References Cited

U.S. PATENT DOCUMENTS

| | | | |
|---|---|---|---|
| 3,638,652 | 2/1972 | Kelley | 128/305 |
| 3,952,747 | 4/1976 | Kimmell, Jr. | 128/303 R |
| 4,351,466 | 9/1982 | Noiles | 227/8 |

FOREIGN PATENT DOCUMENTS 266139  4/1973  U.S.S.R. ........................... 128/334 R

Primary Examiner—John D. Yasko
Assistant Examiner—Gene B. Kartchner
Attorney, Agent, or Firm—John E. Nathan; Robert R. Jackson; Richard A. Inz

[57] ABSTRACT

An apparatus for applying surgical fasteners to tissue is disclosed. The apparatus includes an actuator, an applicator section for applying the fasteners and a transversely flexible shaft connecting the applicator and the actuator. The actuator and applicator preferably each contain a hydraulic fluid chamber. The chambers communicate via a hydraulic line contained in the flexible shaft. Actuation of the instrument causes movement of a piston in the applicator fluid chamber, which causes application of the fasteners. A similar second hydraulic system is preferably provided for adjusting the axial position of an anvil used to clinch the fasteners. The two hydraulic control systems are operable wholly independently of each other, permitting precise control of the anvil pressure on the tissue.

13 Claims, 6 Drawing Figures

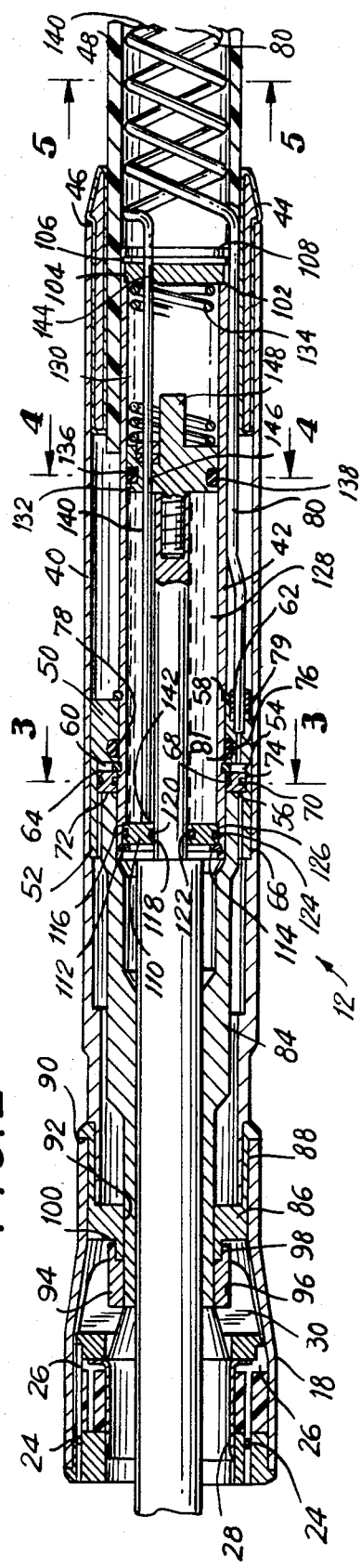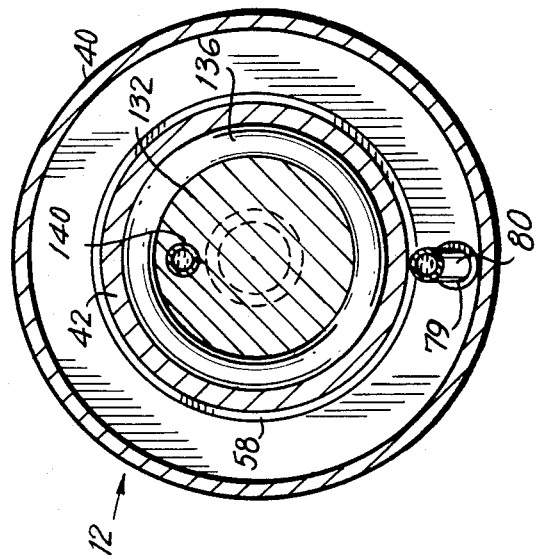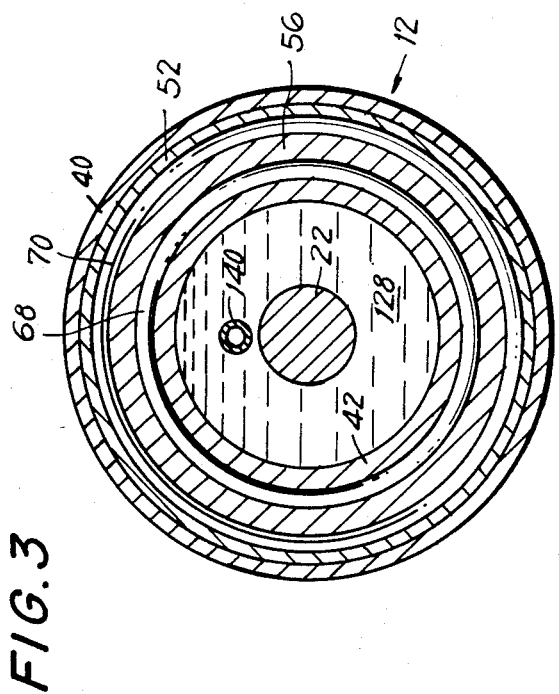

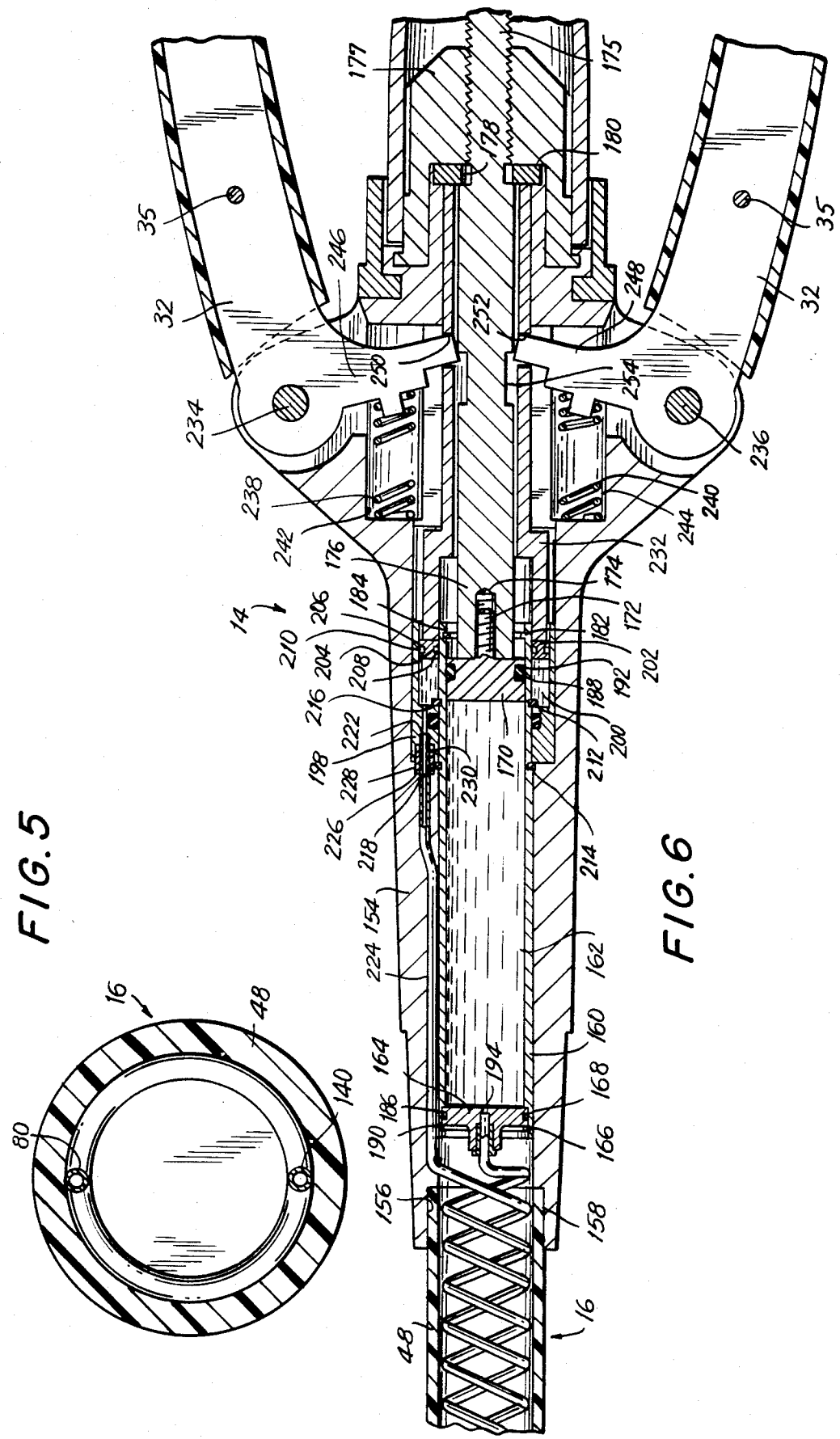

FLEXIBLE, HYDRAULICALLY ACTUATED DEVICE FOR APPLYING SURGICAL FASTENERS

BACKGROUND OF THE INVENTION

This invention relates to a surgical stapler apparatus, and more particularly to a surgical stapler apparatus having a transversely flexible shaft intermediate the portion of the apparatus which performs the stapling (hereinafter the "applicator portion") and the actuator portion of the apparatus. (For simplicity, discussion hereinafter will largely be confined, in terms, to surgical staplers, but it is to be understood that the scope of the invention includes apparatus for applying any type of surgical fasteners.)

There are several known types of surgical staplers in which the stapling takes place at a location relatively remote from the location at which the stapler is held and actuated by the operator. Examples of such staplers are the linear closure surgical staplers shown in U.S. Pat. No. 3,494,533, issued Feb. 10, 1970, to Green et al., and commonly assigned herewith, and the circular anastomosis surgical staplers shown in U.S. Pat. No. 4,304,236, issued Dec. 8, 1981, to Conta et al., and commonly assigned herewith. Typically, in instruments of the types shown in these patents, tissue to be stapled is clamped between an anvil assembly and a staple holding assembly, both of which are located at the distal end of the instrument. The clamped tissue is stapled by driving one or more staples from the staple holding assembly so that the ends of the staples pass through the tissue and are clinched by being driven against the anvil assembly. The forces required to operate the instrument are applied by the operator of the instrument to an actuator mechanism located at or near the proximal end of the instrument. The applicator and actuator portions of the instrument are joined by a longitudinal connecting shaft along which the actuating forces are transmitted to the distal applicator. This type of construction, including relatively widely spaced distal and proximal portions, may be employed for any of several reasons, such as the relative inaccessibility of the tissue to be stapled, or the need to see the tissue well during stapling.

In some applications of instruments of the types mentioned above, it may be desirable for the longitudinal shaft joining the distal and proximal portions of the apparatus to have at least a section that can be bent in a direction transverse to the longitudinal axis of the instrument. This may facilitate placing the instrument in particular body structures or reaching remote or relatively inaccessible stapling sites, or it may allow the staples to be applied at various angles relative to the actuator portion of the instrument.

The approach taken in the present invention is to transmit only a small force hydraulically along the flexible shaft and to use that force to generate a larger force in the applicator to apply the staples to the tissue. By localizing the large stapling force in one end of the apparatus, and making the force transmitted along the flexible shaft sufficiently small, the flexible shaft can be kept from straightening significantly during application of the staples.

In instruments employing anvils against which the fasteners are clinched, the tissue is typically clamped between the anvil and a cooperating portion of the instrument with a force determined by the tissue thickness and by the gaps between the anvil and the cooperating element. It is desirable to be able to control the pressure on the tissue by adjusting the gap. In one known device, disclosed in U.S. Pat. No. 3,638,652, issued Feb. 1, 1970, to Kelley, the tissue to be stapled is held between the staple-holding unit and the clincher, and the staples are applied by means of pulling the staple holder toward the anvil. The pressure on the tissue at each instant depends almost entirely on the force exerted on the tissue by the staples. It is desirable, however, to control the clamping pressure entirely independently of the fastener application process.

SUMMARY OF THE INVENTION

It is the principal object of the invention to provide a transversely flexible instrument for applying surgical fasteners to tissue.

Another object of the invention is to provide such an instrument in which the large forces required for applying the fasteners are localized in one end of the device.

Another object of the invention is to provide such an instrument having a hydraulic actuation system.

Still another object of the invention is to provide such an instrument that is at least substantially equally flexible in any transverse direction.

Another object of the invention is to provide a flexible surgical stapling instrument having means for clamping tissue between an anvil and a staple cartridge, in which the gap between the anvil and the cartridge when in the clamped portion and the clamping action itself are controllable hydraulically and entirely independently of the fastening operation.

The present invention is an instrument for applying surgical fasteners to tissue, comprising an applicator portion and an actuator portion joined by a transversely flexible shaft. A conventional staple holder, containing the fasteners and pushers to eject the fasteners, is disposed at the distal end of, and is preferably an integral part of, the applicator, which includes means for cooperating with the pushers to eject the fasteners. Preferably, the applicator and the actuator each comprise a fluid chamber containing a piston, and the flexible shaft contains a hydraulic line connecting the interiors of the chambers to define a closed hydraulic system filled with an incompressible hydraulic fluid. Movement of the actuator piston causes corresponding movement of the applicator piston, which is connected to the device cooperating with the pushers to eject the fasteners. The shaft is preferably made flexible by shaping the hydraulic line as a helix and housing the helix in a cylindrical sheath of a flexible material.

In the preferred embodiment, the apparatus of the invention also comprises a second closed hydraulic system similar to the first, including pistons housed in additional fluid chambers located respectively in the actuator and applicator portions and connected by a second preferably helical hydraulic line in the flexible shaft. The second hydraulic system is for moving an anvil support rod in the applicator distally and proximally to clamp tissue between the staple holder and an anvil mounted on the support rod. One of the pistons of the second hydraulic system is preferably biased to urge the anvil away from the staple holder. The two hydraulic lines may be intertwined to define a double helix, and the two fluid chambers at each end of the instrument may be concentric, one being cylindrical and the other annular.

The hydraulic fluid is preferably a sterile 0.9% saline solution, to reduce the risk of infection in the event of a leak of the hydraulic fluid.

Other objects and features of the invention will become clear upon consideration of the following detailed description of one preferred embodiment, taken in conjunction with the accompanying figures, in which like reference characters indicate like elements throughout.

BRIEF DESCRIPTION OF THE FIGURES

FIG. 2 is a longitudinal cross-section of the applicator portion of the embodiment of FIG. 1, taken from section line 2—2 of FIG. 1.

FIGS. 3, 4 and 5 are transverse cross-sectional views taken from section lines 3—3, 4—4 and 5—5 of FIG. 2, respectively.

FIG. 6 is a longitudinal cross-section of the actuator portion of the embodiment of FIG. 1, taken from section line 6—6 of FIG. 1.

DETAILED DESCRIPTION OF THE PREFERRED EMBODIMENT

Figure 1:
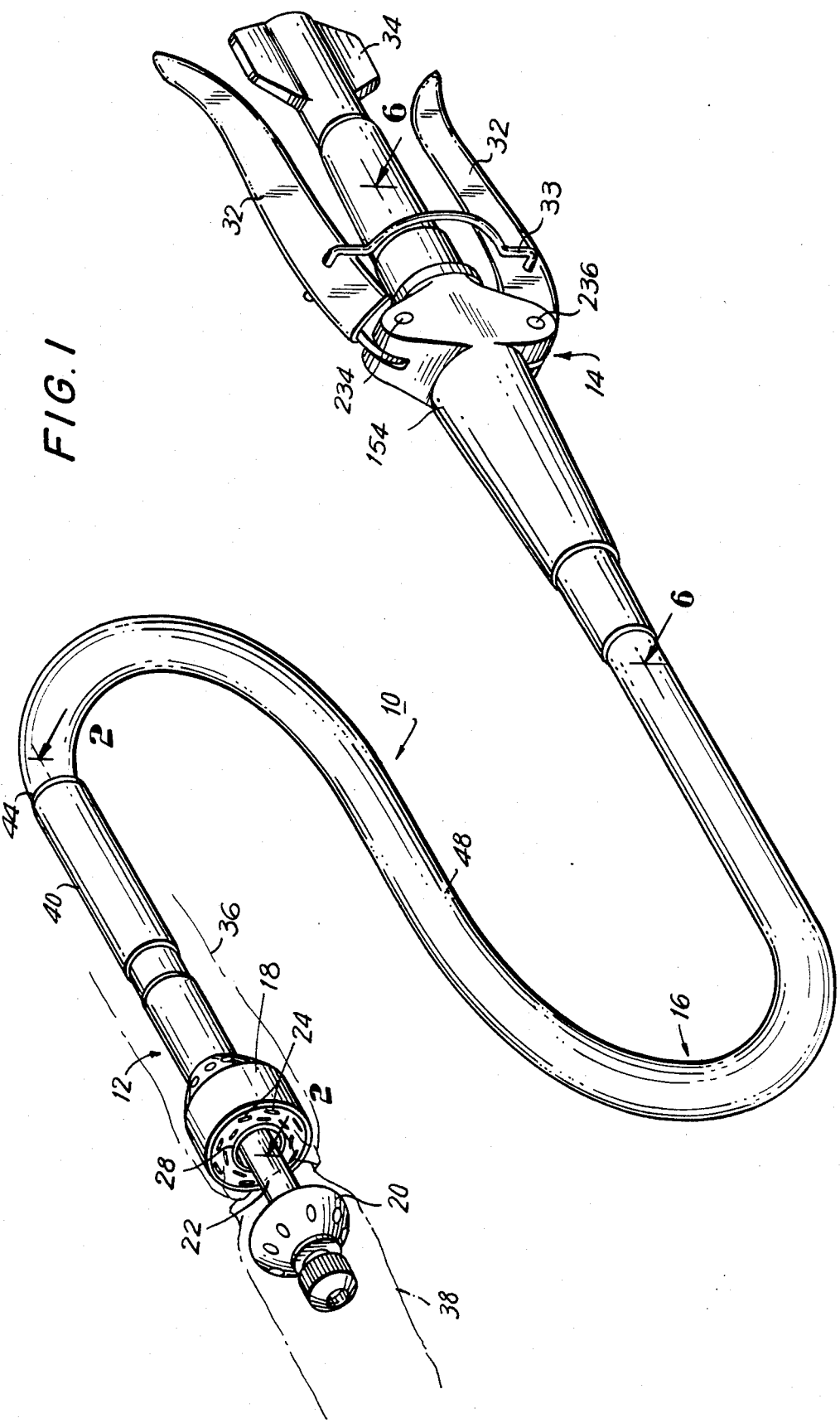
FIG. 1 is a perspective view of the preferred embodiment of the invention.

By way of illustration only, the invention is herein described in detail and depicted with reference to one preferred embodiment, viz. a disposable instrument 10 for end-to-end anastomoses ("EEA").

As shown in FIG. 1, the instrument 10 of the invention has three principal sections: an applicator portion 12 at the distal end of the instrument 10, an actuator portion 14 at the proximal end, and a flexible shaft 16 joining the applicator 12 and the actuator 14.

A conventional staple holder 18 is disposed at the distal end of the applicator 12 and an anvil 20 at the distal end of an axially movable anvil support rod 22. The staple holder 18 contains two concentric annular arrays of staples 24 (see FIG. 2) the points of which are directed toward corresponding depressions, or buckets (not shown), defined in the proximal surface of the anvil 20. Each staple 24 is disposed to be axially movable by means of a respective staple pusher 26. An annular knife 28 is disposed in the cartridge 18 inside the rings of staples 24 and is axially movable in tandem with the staple pushers 26. The knife 28 and the staple pushers 26 are mounted on a collar 30 that is received for axial movement in the housing of the cartridge 18. The anvil 20 is keyed to the anvil support rod 22, which is keyed to the body of the applicator 12, at the distal end of which the staple holder 18 is irrotatably disposed. This arrangement, as is well known, maintains the proper circumferential orientation of the staples 24 relative to the anvil buckets.

The actuator 14 has two opposing scissors-like handles 32 and an anvil control knob or wing-nut handle 34 for controlling the axial movement of the anvil 20 relative to the staple holder 1B. To prevent accidental firing of the instrument 10, a wire 33, whose ends are received in holes 35 provided for them in handles 32, locks the handles 32 in the unfired position. When the instrument is to be actuated, the surgeon removes the wire 33.

The general manner of use of the instrument 10 is as follows. The applicator 12 is inserted, preferably via a natural orifice, into the lumen of an organ section 36 (shown in FIG. 1 in phantom) that is to be anastomosed to another organ section 38 (shown in phantom). In FIG. 1, the organ sections 36, 38 are two portions of the colon that are to be joined end-to-end. For the insertion, the flexible shaft 16 is bent into a shape suitable for the particular patient. When the applicator 12 reaches the location at which the anastomosis is to be made, the surgeon extends the anvil 20 into the lumen of the more remote organ section 38 by means of the wing-nut handle 34. While the anvil 20 is held in the extended position, the surgeon places purse-string sutures (not shown) near the ends of the organ sections 36, 38 in a well-known manner and pulls the sutures tight. The anvil 20 is then retracted in a manner described below to clamp the ends of the organ sections 36, 38 together between the anvil 20 and the staple holder 18. The surgeon then actuates the instrument 10 by squeezing the handles 32. This causes the applicator 12 to eject the staples 24 from the staple holder 18 axially and through the two layers of tissue, and forces the staples against the anvil 20 to clinch them. As the staples 24 are ejected, the annular knife 28 also moves distally through the two layers of tissue, cutting out from each of the two organ sections 36, 38 an annulus of tissue radially inside the ring of staples joining the organ sections 36, 38. The surgeon then withdraws the instrument 10 through the aperture in the proximal organ section 36 through which it was inserted.

FIGS. 2-4 show the applicator portion 12 in greater detail. The applicator 12 comprises a cylindrical outer housing 40. A cylindrical inner housing 42 is disposed in the outer housing 40 coaxially therewith. An adapter sleeve 44 is received snugly in and protrudes from the proximal end of the outer housing 40. The wall of the protruding part of the adapter sleeve 44 is thicker than the portion received in the outer housing 40 and defines a shoulder 46 on which the proximal end of the outer housing 40 sits. The flexible shaft 16 comprises a flexible outer sheath 48 that is snugly received between, and is secured to, the inner housing 42 and the adapter sleeve 44.

The distal end of the inner housing 42 is spaced from the outer housing 40 by a spacer collar 50 having an L-shaped cross-section. The stem 52 of the L lies against the interior surface of the outer housing 40 and, with the inner housing 42, defines an annular chamber 54 wherein an annular piston 56 is slidably received for axial movement. Annular stops 58, 60 disposed in circumferential grooves 62, 64 in the outer surface of the inner housing 42 maintain the spacer collar 50 stationary. A shoulder 66 provided in the inner surface of the outer housing 40 receives the distal end of the spacer collar 50. The distal stop 60 also maintains a minimum axial spacing between the piston 56 and the spacer collar 50. Seals between the piston 56, on one hand, and the inner housing 42 and the spacer collar 50, on the other hand, are provided by O-rings 68 and 70 disposed respectively in inner and outer circumferential grooves 72 and 74 in the piston 56. An additional O-ring 76 disposed in a groove 78 in the inner circumferential surface of the spacer collar 50 provides a proximal seal for the fluid chamber 54. A hydraulic line 80 has its distal end fixedly received in a through aperture 62 in the proximal surface of the spacer collar 50. The proximal end of a generally cylindrical staple sleeve 84, which is received coaxially about the anvil support rod 22, is secured to the distal face of the piston 56. As noted previously, the staple sleeve 84 is keyed in known manner to the anvil support rod 22 to permit sliding movement of the anvil support rod 22 and the staple sleeve 84 relative to each other in an axial direction only.

A cap 86 having a cylindrical skirt 88 secured to the exterior of the distal end of the outer housing 40 defines a shoulder 90 to receive the staple holder 18, which is received over the skirt 88. The anvil support rod 22 and the staple sleeve 84 pass through a bore 92 in the cap 86. A collar 94 secured to the distal end of the staple sleeve 84 is received in a recess 96 in the proximal surface of the staple pushing collar 30 in the staple holder 18. An annular axial flange 98 on the distal surface of the cap 86 is received in a recess 100 in the proximal surface of collar 94 when the instrument 10 is in its unfired state, depicted in FIG. 2. The introduction of sufficient hydraulic fluid into the annular chamber 54 via the hydraulic line 80 forces the staple sleeve 84 distally, ejecting the staples 24 from the staple holder 18 and advancing the annular knife 28 as described above.

The proximal end of the inner housing 42 is plugged by an end wall 102 held in place axially by a shoulder 104 defined in the interior surface of the inner housing 42 and an annular stop 106 received in a circumferential groove 108 provided in the wall of the inner housing 42. A similar wall 110 closes the distal end of the inner housing 42 and is retained in place by an annular stop 112 received in a groove 114 and by a shoulder 116 defined in the inner surface of the inner housing 42. The anvil support rod 22 is slidably received in a central bore 118 in the distal end wall 110. A seal between the bore 118 and the anvil support rod 22 is provided by an O-ring 120 received in a circumferential groove 122 in the bore 118. An O-ring 124 in a similar groove 126 in the outer peripheral surface of the distal end wall 110 provides a seal between the distal end wall 110 and the inner housing 42.

The interior of the inner housing 42 is divided axially into two compartments 128, 130 by a plug 132 slidably received in the inner housing 42 and secured to one end of a spring 134 whose other end rests on the proximal end wall 102. An O-ring 136 disposed in a circumferential groove 138 provides sealing contact between the sliding plug 132 and the inner housing 42. The proximal end of the anvil support rod 22 is fixed, as by threads, to the distal surface of the plug 132. The spring 134 biases the sliding plug 132 and the anvil suppor rod 22 distally. A second hydraulic line 140 enters the chamber 128 defined between distal end wall 110 and sliding plug 132 and has one end 142 open near the proximal surface of distal end wall 110. Preferably, hydraulic line 140 passes through apertures 144, 146 in the proximal end wall 102 and the sliding plug 132, being secured to the former and slidably and sealingly received in the latter.

Forcing a hydraulic fluid into the chamber 128 via hydraulic line 140 forces the sliding plug 132 and the anvil support rod 22 in a proximal direction. To indicate the axial position of the anvil 20 relative to the applicator 12, in a manner described in commonly-assigned U.S. Pat. No. 4,379,457, issued Apr. 12, 1983, to Grauener et al., the entire disclosure of which is incorporated herein by reference, an axial stud 148 on the proximal surface of the sliding plug 132 can, if desired, be received securely in one end of a flexible tube (not shown) passing through an aperture (not shown) provided for it in the proximal end wall 102 and extending along the axis of the flexible shaft 16, inside the flexible sheath 48, from the applicator 12 to the actuator 14 to move a visible indicator in the handle of the actuator 14. The position of the indicator would show the axial position of the anvil 20.

The flexible shaft 16, as already noted, comprises the flexible sheath 48 housing the hydraulic lines 80, 140 (see FIG. 5). The portions of hydraulic lines 80, 140 in the sheath 48 are preferably helical and are arranged to form a double helix, i.e., the hydraulic lines 80, 140 coil in the same sense (right-handed or left-handed), have the same pitch and are intertwined. The hydraulic lines 80, 140 are preferably made of nylon or stainless steel or of another material sufficiently strong to make the helical lines 80, 140 self-supporting. The helical shape of the lines 80, 140 makes the shaft assembly 16 sufficiently flexible in all transverse directions to enable the shaft 16 to be bent into a shape suited to the particular patient and the operation in question. As a result, the instrument 10 of the invention can be inserted much farther into an organ via a natural orifice, without a special incision being necessary to insert the instrument, than is possible with a rigid instrument.

As shown in FIG. 6, the actuator portion 14 of the instrument 10 comprises a generally cylindrical outer housing 154 having a coaxial bore 156. The distal end of the bore 156 is enlarged to define a shoulder 158 on which the proximal end of the flexible sheath 48 of the flexible shaft 16 is seated. A reservoir sleeve 160 is disposed in the bore 156, slightly spaced axially from the proximal end of the sheath 48, to define a reservoir 162 for the hydraulic fluid used to move the anvil support rod 22. The distal end of the reservoir 162 is defined by a fixed distal plug 164 held in place by means of a distal annular stop 166 and a shoulder 168 provided in the inner surface of the bore 156. The proximal end of the reservoir 162 is defined by a piston 170 slidably received in the reservoir sleeve 160. The proximal side of the piston 170 has a threaded axial stud 172 that is received in a mating threaded axial bore 174 in the distal end of an axial shaft 176 whose proximal end is secured to the wing-nut handle 34. The proximal portion of the shaft 176 is threadedly and rotatably received in a bore 175 in a collar 177 secured to the actuator housing 154. Rotation of the wing-nut handle 34 advances the shaft 176 distally due to the threaded engagement of the shaft 176 and collar 177.

The proximal limit of travel of the piston 170 is defined by a shoulder 178 of the shaft 176, which cooperates with an annular stop 180 (disposed axially between collar 177 and housing 154) to limit the piston travel, and by another annular stop 182 disposed in a circumferential groove 184 in the interior surface of the reservoir sleeve 160. Both the distal plug 164 and the piston 170 are sealed to the reservoir sleeve 160 by means of O-rings 186, 188 disposed in circumferential grooves 190, 192 in the plug 164 and the piston 170, respectively. The proximal end of the hydraulic line 140 preferably passes into an axial through-aperture 194 in the plug 164, to which line 140 is fixed.

A generally annular spacer collar 198 having an L-shaped cross-section and disposed between the reservoir sleeve 160 and the actuator housing 154 defines an annular fluid chamber 200 the proximal side of which is defined by an annular piston 202 slidably disposed between the reservoir sleeve 160 and the stem of the L. O-rings 204, 206 in respective grooves 208, 210 in the inner and outer circumferential surfaces of the plug 202 provide seals for the annular fluid chamber 200. The spacer collar 198 is fixed in place by means of annular stops 212, 214 received in grooves 216, 218 in the outer surface of the reservoir sleeve 160. A through-aperture 222 in the distal end of spacer collar 198 receives the proximal end of the hydraulic line 80 fixedly. The proximal portion of the hydraulic line 80, after leaving the proximal end of the flexible shaft 16, extends through a passage 224, in which it fits snugly, provided for it in the body of the actuator housing 154, generally parallel to the bore 156. A plug 226 fixed in a bore 228 in the distal face of the spacer collar 198 receives the hydraulic line 80 in a through-hole 230, which communicates with the through-hole 222.

An actuator sleeve 232, mounted coaxially in the actuator housing 154 for axial sliding motion, has its distal end secured to the annular piston 202. The actuator housing 154 has two symmetrically placed pivot pins 234, 236 on each of which is pivotally mounted one of the two handles 32. A respective spring 238, 240 disposed in a respective parallel axial bore 242, 244 engages a portion of each handle 32 radially inward of the pivot point to urge the free ends of the handles 32 outward, i.e., away from the actuator housing 154. Radially inward from the portion of each handle 32 that engages a spring 238, 240 is a tab 246, 248 whose end is received in a respective slot 250, 252 in the actuator sleeve 232. When the operator squeezes the handles 32 together, the tabs 246, 248 cooperate with the slots 250, 252 to drive the actuator sleeve 232 and the annular piston 202 distally, forcing hydraulic fluid from the annular fluid chamber 200 into the hydraulic line 80 to effect stapling as described above.

An annular groove 254 is provided in the surface of the shaft 176 to accommodate the inward swing of the tabs 246, 248 as the handles 32 are squeezed. The proximal end of the shaft 176 is threadedly fixed in the interior of the wing-nut handle 34. Rotation of the wing-nut handle 34 moves the piston 170 and, via the hydraulic line 140, moves the anvil support rod 22.

It is believed that the operation of the instrument 10 will now be clear. After retracting the anvil 20 against the cartridge 18 by rotating the wing-nut handle 34, the surgeon inserts the distal end of the instrument 10 into the lumen of one of the organ sections 36, 38 to be fastened together. The anvil 20 is then extended by rotation of the wing-nut handle 34 to retract the shaft 176, allowing the spring 134 in the applicator 12 to extend the anvil support rod 22. The purse-string sutures are then made and pulled tight, after which the wing-nut handle 34 is rotated in the opposite direction to retract the anvil 20 to clamp the tissue against the cartridge 18 without crushing the tissue. The friction between the collar 177 and the shaft 176 is sufficient to retain the anvil 20 in the retracted position during stapling. The hydraulic fluid used in both hydraulic systems is incompressible, and therefore cannot act like a spring to permit accidental extension of the anvil 20, even during stapling. After removing the lock wire 33, the surgeon squeezes the handles 32 together to force hydraulic fluid from the annular fluid chamber 200, through the hydraulic line 80 and into annular fluid chamber 54, moving the staple sleeve 84 distally, stapling the tissue and excising an annulus of tissue from within the ring defined by the staples. When the handles 32 are released, they are forced outward by the springs 238, 240, drawing fluid back from the applicator 12 to the annular reservoir 200 in the actuator 14. The instrument 10 is then withdrawn from the patient.

Those skilled in the art will recognize that the independent hydraulic system for adjusting the anvil position permits the surgeon to control the clamping pressure on the tissue wholly independently of the fastener application process.

The hydraulic fluid used in both hydraulic systems is preferably sterile 0.9% saline solution. This reduces the risk of infection in the event of a leak of the hydraulic fluid.

Those skilled in the art will recognize that the mechanical advantage of each of the hydraulic systems can be selected as desired by proper selection of the ratio of the effective areas of the pistons in the actuator and applicator fluid chambers of the hydraulic system in question. For example, by making the area of the distal face of annular piston 202 one-third the area of the proximal face of annular piston 56, a mechanical advantage of three to one is obtained, so that the force the surgeon must exert on piston 202 by squeezing the handles 32 is one-third the force the applicator piston 56 must exert on the staple pushers 26 and the knife 28 to staple and cut the tissue.

The instrument 10 described above is a disposable one, in which the staple holder 18 and anvil 20 are integral parts of the instrument. If desired, however, the instrument could be made reusable. In this case, the integral anvil 20, staple holder 18, staple pushers 26, and knife 28 would be replaced with a disposable cartridge of conventional design. This variation is also within the scope of the invention.

Although the invention has been particularly described with reference to one preferred embodiment, many modifications and variations thereof will now be apparent to those skilled in the art; accordingly, the scope of the present invention is to be determined not by reference to the illustrative details described herein, but only by the terms of the appended claims.

I claim:

1. An apparatus for applying a surgical fastener to tissue, said apparatus comprising:
   applicator means for applying a surgical fastener to tissue, said applicator means including means for driving a surgical fastener in a predetermined direction to apply the fastener to tissue; said applicator means further including anvil support means for supporting an anvil for clinching a fastener driven by said driving means and for clamping tissue to which a fastener is to be applied; said applicator means having a distal end and a cooperating element disposed at said distal end of said applicator means for clamping tissue between the anvil and said cooperating element;
   actuator means for actuating said applicator means to drive a fastener in said predetermined direction;
   shaft means joining said actuator means and said applicator means, and comprising a first hydraulic line containing hydraulic fluid for hydraulically transmitting an actuation force from said actuator means to said applicator means to cause said applicator means to drive a fastener in said predetermined direction; said shaft means being sufficiently flexible to bend, in a direction transverse to its length, during insertion into a body channel, to conform to the configuration of said body channel into which the apparatus is inserted for the particular surgical operation, and sufficiently stiff to retain such configuration during application of a fastener; and
   means for moving an anvil supported by said anvil support means and for adjusting the distance between the anvil and said cooperating element preparatory to applying a fastener;

said anvil moving means comprising a control mechanism disposed in said actuator means, and means disposed in said shaft means for transmitting a force hydraulically from said control mechanism to said anvil support means for moving said anvil support means.

2. The apparatus of claim 1, wherein said actuating means comprises a fluid chamber and a piston disposed in said fluid chamber for generating the actuation force to be transmitted hydraulically to said applicator means via said shaft means.

3. The apparatus of claim 1, wherein said applicator means comprises a fluid chamber and a piston disposed in said fluid chamber for cooperating with said driving means to drive a fastener in said predetermined direction responsive to the actuation force transmitted hydraulically from said actuator means via said shaft means.

4. The apparatus of claim 1, further comprising holder means containing a surgical fastener to be driven by said driving means, and an anvil supported by said anvil support means.

5. The apparatus of claim 4, wherein said holder means and said anvil are integral parts of said applicator means.

6. The apparatus of claim 4, wherein said holder means and said anvil are disposable elements; said anvil being removably disposed on said anvil support means; and said applicator means further comprising means removably receiving said holder means.

7. The apparatus of claim 1, wherein said transmitting means in said shaft means comprises a second hydraulic line.

8. The apparatus of claim 7, wherein said hydraulic lines are both helical and define a double helix.

9. The apparatus of claim 7, wherein said actuator means comprises a first fluid chamber containing hydraulic fluid and a first piston for moving hydraulic fluid from said first fluid chamber into said first hydraulic line for transmitting the actuation force from said actuator means to said applicator means, and wherein said control mechanism of said anvil moving means comprises a second fluid chamber containing hydraulic fluid and a second piston for moving hydraulic fluid from said second fluid chamber into said second hydraulic line for transmitting a force hydraulically via said shaft means to said applicator means for moving said anvil support means.

10. The apparatus of claim 9, wherein said first fluid chamber is approximately annular and surrounds at least a portion of said second fluid chamber.

11. The apparatus of claim 1, wherein said applicator means comprises an applicating fluid chamber and an applicating piston for driving a fastener in said predetermined direction responsive to said actuation force, and wherein said anvil moving means comprises an anvil-moving fluid chamber disposed in said applicator means and an additional piston for moving said anvil support means responsive to a force hydraulically transmitted from said control mechanism.

12. The apparatus of claim 11, wherein said applicating fluid chamber is approximately annular and surrounds at least a portion of said anvil-moving fluid chamber.

13. The apparatus of claim 1, further comprising means biasing said anvil support rod in a distal direction.

* * * * *